United States Patent
Pandey et al.

[19]

[11] Patent Number: 5,817,510
[45] Date of Patent: Oct. 6, 1998

[54] DEVICE AND METHOD FOR EVALUATING MICROORGANISMS

[75] Inventors: Ramesh C. Pandey, Highland Park; Swami Nathan, Piscataway, both of N.J.

[73] Assignee: Xechem International, Inc., New Brunswick, N.J.

[21] Appl. No.: 747,622

[22] Filed: Nov. 13, 1996

Related U.S. Application Data

[63] Continuation of Ser. No. 394,155, Feb. 24, 1995, abandoned.

[51] Int. Cl.[6] .................................................. C12M 3/00
[52] U.S. Cl. ........................................ 435/305.3; 422/102
[58] Field of Search ........................... 435/286.5, 288.3, 435/288.4, 305.1, 305.2, 305.3, 305.4; 422/100, 102

[56] References Cited

U.S. PATENT DOCUMENTS

| | | |
|---|---|---|
| D. 223,874 | 6/1972 | Ellis . |
| D. 264,810 | 6/1982 | Voltmann ................................. D9/341 |
| D. 338,965 | 8/1993 | Glanz et al. ............................ D24/223 |
| 3,278,393 | 10/1966 | Bahn . |
| 3,725,004 | 4/1973 | Johnson et al. . |
| 3,769,936 | 11/1973 | Swanson et al. . |
| 3,936,356 | 2/1976 | Janin . |
| 4,012,288 | 3/1977 | Lyman et al. . |
| 4,038,149 | 7/1977 | Liner et al. . |
| 4,235,963 | 11/1980 | Hansen ...................................... 435/30 |
| 4,304,865 | 12/1981 | O'Brien et al. ........................... 435/240 |
| 4,385,123 | 5/1983 | Kang et al. . |
| 4,495,289 | 1/1985 | Lyman et al. . |
| 4,690,896 | 9/1987 | Brüsewitz et al. . |
| 4,801,547 | 1/1989 | Rosenberg . |
| 4,863,689 | 9/1989 | Leong et al. ............................... 422/52 |
| 4,952,510 | 8/1990 | Gabridge . |
| 5,358,871 | 10/1994 | Stevens et al. . |
| 5,462,860 | 10/1995 | Mach ........................................ 435/34 |

FOREIGN PATENT DOCUMENTS

| | | | |
|---|---|---|---|
| 3136251A1 | 4/1983 | Germany .......................... C12M 1/18 |
| WO9118085 | 11/1991 | WIPO .............................. C12M 1/18 |

OTHER PUBLICATIONS

VWB Scientific catalog, "Six Well, Flat Bottom Plates, Falcon," item #62406–161, p. 1619 (1989).
The Lab Book Catalog, "Cell Wells," pp. 226 & 227 (1983).
Difco Product Catalog for Microbiology (Jan. 1994).

*Primary Examiner*—David A. Hedding
*Attorney, Agent, or Firm*—Banner & Witcoff Ltd.

[57] ABSTRACT

A device for culturing and identifying microorganisms comprising a transparent vessel with a sealable cover, a nutrient substrate carrier that can be coated with a novel growth medium and a method of using the same are disclosed. A plurality of nutrient substrates may be applied to the nutrient substrate carrier and separated into distinct zones so that a variety of microorganisms may be tested for. The method comprises innoculating the nutrient substrate with a liquid sample and incubating the nutrient substrate so that the microorganisms can be identified by visual observation of the color change of the substrate through the transparent vessel.

4 Claims, 2 Drawing Sheets

DEVICE AND METHOD FOR EVALUATING MICROORGANISMS

This is a continuation of application Ser. No. 08/394,155, filed Feb. 24, 1995, now abandoned.

FIELD OF THE INVENTION

The present invention relates generally to a method of culturing and identifying microorganisms and more particularly to a method of culturing and identifying multiple samples of microorganisms and a system and apparatus wherein a sample can be inoculated into media without removing the lid of the apparatus containing the media, thereby reducing contamination of the media.

Tissue culture dishes and culturing methods known in the prior art disclose methods for collecting and growing microorganisms in various devices containing various media. For example, U.S. Pat. No. 4,012,288 describes a tissue culture cluster dish having a removable lid and a base with the a plurality of wells formed therein. A protrusion extending upwards from the base allows for atmospheric communication between the well interior and the outside of the cluster dish. The tissue culture cluster dish is made of clear plastic to allow for the facile identification of microorganisms.

U.S. Pat. No. 2,533,089 discloses a circular petri dish cover with openings so that the solution or solutions to be tested are dropped or poured into the media. There are openings for tubes which lead directly to the media for transfer of the solution or solutions. A second cover is placed over the cover with the openings to reduce contamination.

U.S. Pat. No. 3,769,936 discloses a flat transparent cover for a petri-type dish provided with an externally communicating orifice that may be opened or closed for communication between the exterior and interior of the covered dish without affecting the activity or observation within the dish. This is accomplished by a resilient tape strip which may be transparent. When it is desired to permit communication into the interior, a needle or other probe is inserted with the material to be tested through the orifice to depress the resilient strip, which is moveable to allow the introduction of the substance to be tested. After withdrawal of the needle or probe the resilient strip moves back in place to cover the orifice.

International Patent Application PCT/US91/0304 describes a device for culturing and identifying microorganisms in a liquid sample. The cover of the device has a liquid receiving aperture extending through the top wall for permitting the introduction of a liquid sample into the device. The liquid receiving aperture preferably includes a removable plug to provide a sealed environment. The plug may be removed to permit the sample to be introduced into the device. The inner surface is provided with a pair of diametrically opposed, axially extending recesses therein to provide small air passages through which vapors can escape from within the device when a lower ceiling section of the plug is within the aperture. Further, the aperture can be plugged with a material, such as rubber, or latex, which permits the entry and removal of a syringe or other dispensing instruments to deliver the liquid samples to a filter membrane for testing without requiring removal of the cover. Ribs are provided on the inside wall of the cover to minimize undesirable condensation of vapor on the cover so that one may view the colonies forming in the media.

In view of the prior art, it is believed that a need exists for a single unit in which a variety of microbes may be effectively collected and quickly grown without the need for excessive handling. Further, there is a need for a compact device for the multiple evaluation of microorganisms that can be nested or stacked for the conservation of storage space.

Therefore, it is an object of this invention to provide a device which permits the collection and growth of microorganisms in a sample without the problems of contamination from the outside environment.

It is an object of this invention to provide a quick, facile method of identifying microorganisms. It is also an object of this invention to provide a device which permits the growth and identification of microorganisms in samples to a number of different media.

It is another object of this invention to use simple color change media for the detection of microorganisms.

SUMMARY OF THE INVENTION

According to the invention there is provided a single culture vessel device for culturing and determining the identity of one or more microorganisms from a liquid or dry sample. The device comprises a base with a plurality of wells, a lid, both of which are constructed of transparent plastic material, the lid having an aperature leading to each well in the base so that individual specimens may be inserted into each well containing the same or different media. The invention also comprises a method of culturing and determining the identity of one or more microorganisms using the culture vessel.

DESCRIPTION OF THE PREFERRED EMBODIMENTS

This invention relates to a simple and efficient method for the identification of microorganisms including bacteria. The method generally comprises the steps of culturing and isolating unknown bacteria on a selected media, the media being of specialized formulations to change color for the qualitative identification of the bacteria. Further, the device used with the method of the present invention allows for the identification and culturing of a variety of bacteria while having a compact size to use the least amount of space for storage. The compact nature of the device renders it suitable for use in manned space vehicles.

The unknown bacteria may be in solution or dried. The media may be liquid or lyophilized depending upon the needs of the user. The culturing of the bacteria is done for a sufficient time to produce a reasonable concentration of bacteria in the culturing media so that a color change is effected to show the qualitative identification of the bacteria without microscopic examination.

A filter membrane, such as one manufactured by Gelman having a pore size of 0.45 micron may be attached to the device to localize the bacteria in an area for facile viewing by the user. The accumulation of the bacteria on the filter membrane provides for a concentration of the bacteria and therefore a fairly quick and reliable change of color of the media for easy identification.

While the culturing and identification of the bacteria can be carried out with any suitable equipment and by any convenient method, it is preferable to carry out the culturing and identification of the microorganism in the device of the present invention.

Figures 1, 2, 3, 4:
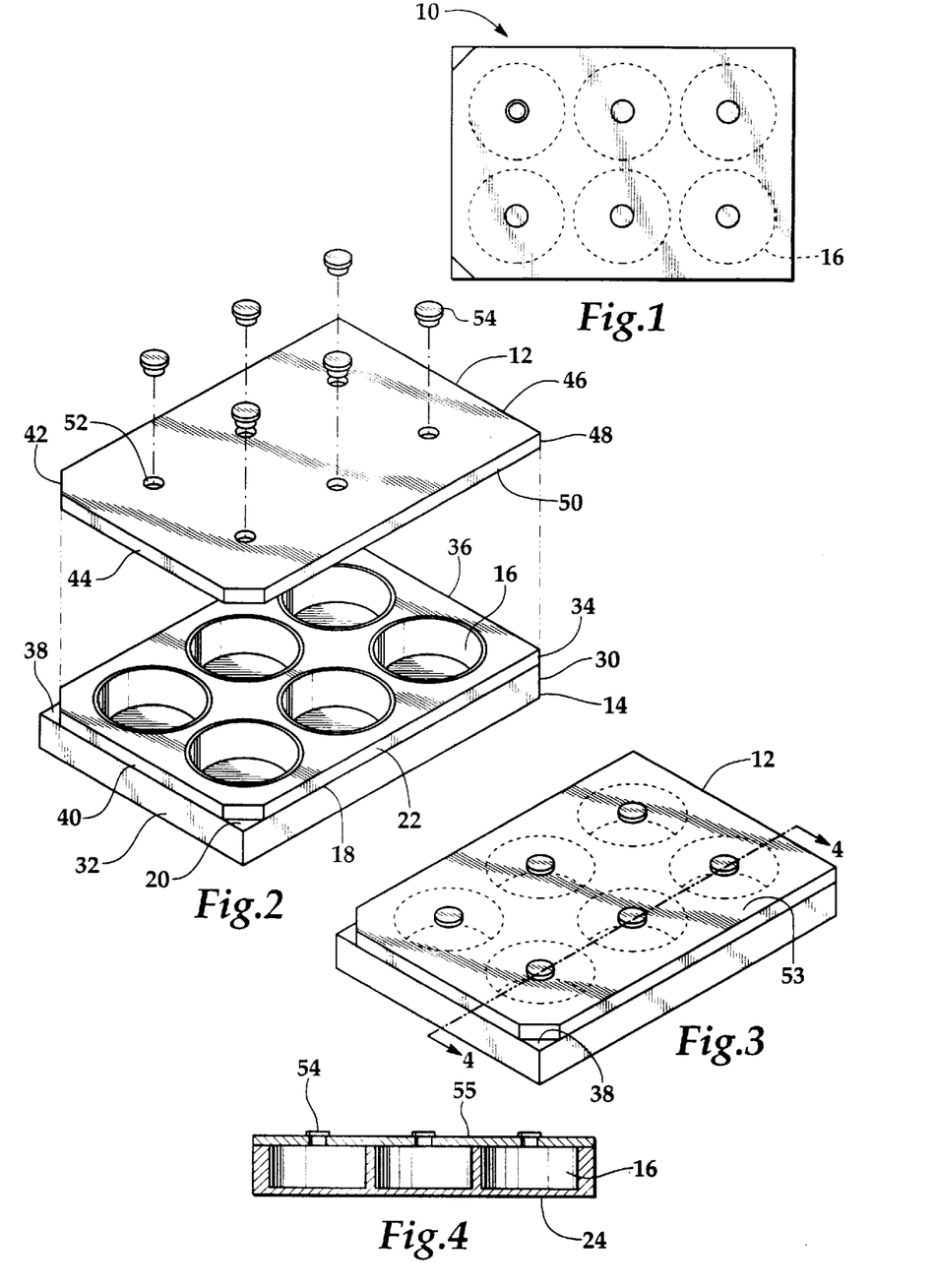
FIG. 1 is a top plan view of the apparatus of the present invention showing six apertures for the entry of microorganisms to the individual wells of the apparatus.
FIG. 2 is an exploded isometric view of the culturing systems shown in FIG. 1.
FIG. 3 is a perspective view of the culturing system in accordance with this invention with the lid placed on the base of the culturing system.
FIG. 4 is sectional view taken along line 4—4 of FIG. 3.
Figures 5, 6, 7:
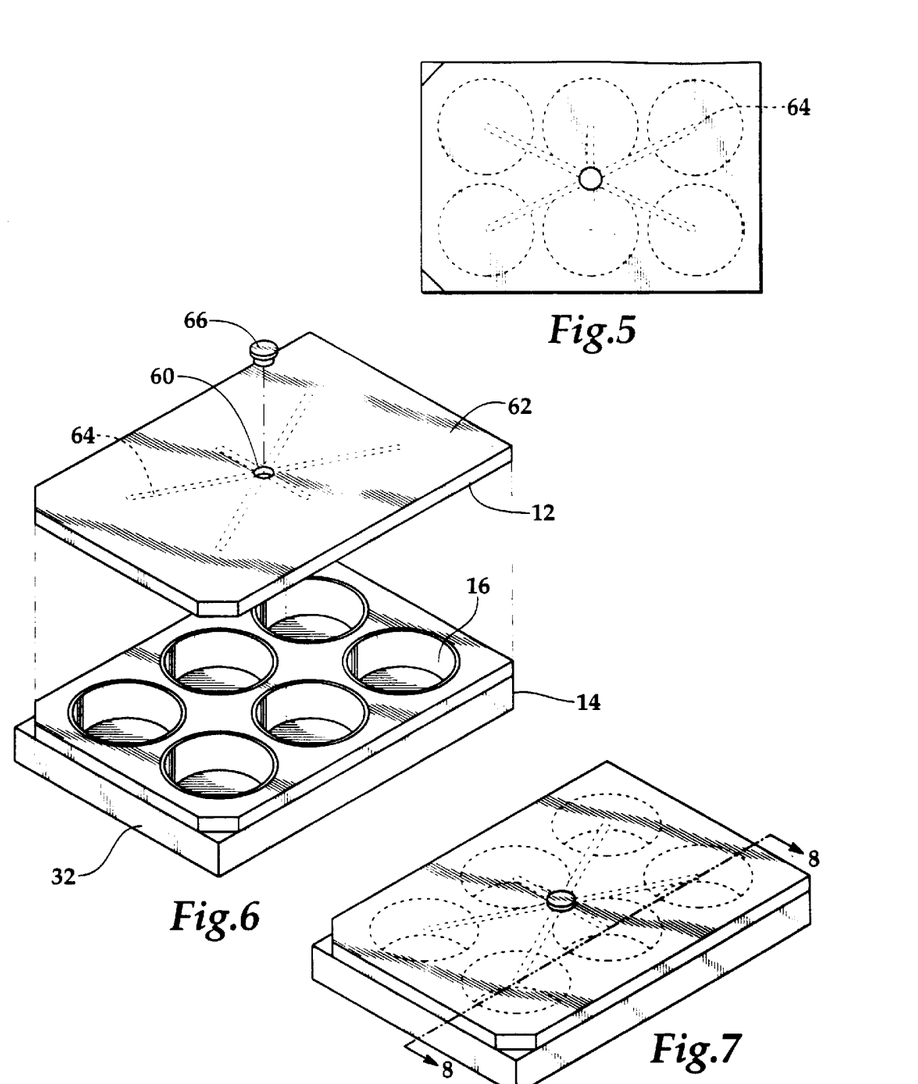
FIG. 5 is a top view of an alternate embodiment of the present invention.
FIG. 6 is an exploded isometric view of an alternative embodiment of the present invention.
FIG. 7 is a perspective view of the culturing system in accordance with this invention with the lid placed on the base of the culturing system with the wells and channels shown in dotted lines.
Figure 8:
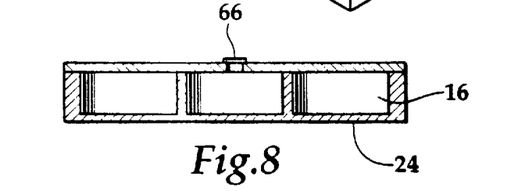
FIG. 8 is sectional view taken along line 8—8 of FIG. 7.

As shown in FIGS. 1 and 2, the device is shown which is constructed in accordance with this invention for use in culturing and identifying microorganisms in a liquid sample or a dry sample. The device comprises, as shown in FIGS. 1–3 and 5–6, openings over each well or a central opening in the lid of the plate, with channels to direct the flow of the sample to each of the wells to allow for the inoculation of samples directly into the various wells through the plate cover.

The device 10 is composed of a removable lid 12 and base 14 both of which are constructed of a transparent plastic material. In the embodiments shown in the drawings, six wells 16 are present in base 14 for the growing of distinct cultures. It is to be understood that more or less wells may be provided in base 14. The base 14 and lid 12 are each constructed of one piece mold plastic material.

The base 14 has a rim 18 and shoulder 20 for supporting lid 12. Rim 18 defines the outer periphery of platform 22 which is supported on base 14. The platform 22 allows for positioning of the wells 16 so that they may be of an adequate depth for receiving the media and specimen. Floor 24 of base 14 is transparent as well as lid 12, for facile viewing of the media and specimen. Floor 24 protects the bottom of the wells 16 from being scratched or marred by the surface of which the device rests.

The base 14 has an identifiable back 30 and front 32. Front 32 defines shoulder 20 which supports lid 12. Further, platform 22 has squared off corners 34 at its back 36 and angled corners 38 at its front 40. This structure not only allows for the identification of the front and back of the base, it allows for the placement of the lid 12 in only one position. Angled corners 38 of platform 22 engage the angled corners 42 of the front 44 of lid 12. The back 46 of lid 12 have squared corners 48 to engage rim 18 and squared corners 34 in back 36 of platform 22. The front 44 of lid 12 with its angled corners 42 engage front 40 of platform 22 at its angled corners 38 while being supported by shoulders 20 in the front 32 of base 14.

The lid 12 has vertical sides 50 which engage rim 18 and shoulder 20 to a height that allows open space between the wells 16 in platform 22 and lid 12. Apertures 52 are strategically placed over wells 16 in lid 12. The apertures 52 allow passage of media and specimens from the exterior side 53 of lid 12 through the lid into wells 16. Media may, of course, be added to wells 16 separately before placement of lid 12 over the platform 22 and base 14. Apertures 52 are positioned over each well 16 to allow for easy access or enable communication to the wells 16 through the lid 12 while reducing the opportunities for contamination which would result be removing and replacing the lid. Plugs 54 are used to seal the apertures 52. Further, if condensation develops on the inside 55 of lid 12, plugs 54 may be removed to allow for evaporation of the condensation to facilitate viewing of the media in the wells 16.

Another embodiment of the present invention, as shown in FIGS. 5 through 8, has a singular centrally positioned aperature 60 in lid 62 for innoculation of samples directly into the media present in wells 16. The lid 62 has a plurality of channels 64 leading from aperture 60. Each channel can be accessed by a sampling probe without contaminating aperture 60 or other channels. The specimen is placed in and directed to one or more channels which may be attached to the inside surface of the lid 62 or bored within lid 62. The channels 64 lead to a position over an individual well 16 where the sample may be introduced into the media in the well 16. Plug 66 is used to seal aperture 60. The arrangement of the present invention allows for the innoculation of media with liquid specimens which reducing the risk of contamination of the media because the lid 62 does not have to be removed for innoculation.

In accordance with the present invention, different media may be used with the same or various specimens in one device to culture and identify microorganisms. For example, with the embodiments shown herein, up to six different media may be utilized in one testing procedure. The liqiud sample can be inserted in each well through aperature 52 or 60. After incubation, the wells can be visually observed to determine the presence of bacteria. The wells 16 may be filled with liquid media before lid 12 or 62 is place over the base 14 or dry media may be inserted before closure. Water for rehydration can be inserted through apertures 50 or 62 to reconstitute the media before introduction of the specimens.

EXAMPLE 1
(Conventional Media which were used for Comparison in this Study)
1. Mannitol salt agar (BBL), widely used medium for *Staphylococcus aureus*.
   Mannitol salt agar (11.1 g) was suspended in 100 ml of deionized water and heated to dissolve completely. It was sterilized in the autoclave for 15 min. at 15 lb. pressure, cooled to 48° C. and poured into petri dishes. The final pH=7.4.
2. Brilliant green agar (BBL), selective medium for *Salmonella sp.*
   Brilliant green agar (5.8 g) was suspended in 100 ml of deionized water and heated to dissolve completely. It was sterilized in the autoclave for 15 min. at 15 lb. pressure, cooled to 48° C. and poured into petri dishes. The final pH=6.9.
3. EMB agar (BBL), widely used medium for Gram negative organisms.
   EMB agar (3.6 g) was suspended in 100 ml of deionized water and heated to dissolve completely. It was sterilized in the autoclave for 15 min. at 15 lb. pressure, cooled to 48° C. and poured into petri dishes. The final pH=7.1.
4. Cetrimide agar (Difco), selective medium for *Pseudomonas aeruginosa*.
   Cetrimide agar (4.53 g) was suspended in 100 ml of deionized water and heated to dissolve completely, then added 1.0 ml of glycerol. It was sterilized in the autoclave for 15 min. at 15 lb. pressure, cooled to 48° C. and poured into petri dishes. The final pH=7.2.
5. Potato malt agar (Difco), widely used medium for fungi.
   Potato malt agar (10.5 g) was suspended in 100 ml of deionized water and heated to dissolve completely. It was sterilized in the autoclave for 15 min. at 15 lb. pressure, cooled to 48° C. and poured into petri dishes. The final pH=7.4.

6. KF Streptococcus agar (Difco), selective medium for Enterococcus.

KF Streptococcus agar (5.64 g) was suspended in 100 ml of deionized water and heated to dissolve completely. It should not be autoclaved. After cooling to 48° C., 1.0 ml of TTC was added to 100 ml of media. The final pH=7.2.

Representative formulations of the nutrient substrates of the present invention are defined in Example 2. These formulations produce enhanced color changes, quick growth and stable formulations.

EXAMPLE 2

(Formulation of present invention)

Mannitol Salt Medium

| Ingredient | Weight/Volume | |
| --- | --- | --- |
| Mannitol | 1.0 g | 1.00% |
| Peptone | 1.0 g | 1.00% |
| Magnesium sulfate | 0.1 g | .10% |
| Phenol red | 0.0025 g | 0.0025% |
| Sodium chloride | 0.75 g | 0.75% |
| Deionized water (pH 7.2) | 100 ml | |
| Gellan gum | 0.6 g | 0.60% |

All the ingredients (mannitol, peptone, magnesium sulfate, phenol red and sodium chloride) were weighed in an analytical balance and dissolved in 100 ml of deionized water by heating and stirring. The pH was adjusted to 7.2. The medium was heated to boiling. Gellan gum (0.6 g) was slowly dispersed to dissolve. Gellan gum is sold under the trademark Gelrite by Schweizerhall, Inc. Piscataway, N.J. The mixture was sterilized for 15 min., cooled to 48° C. and poured 4 ml, 6 ml and 8 ml of media in the designated wells. It was allowed to solidify, After solidification, a sterile filter paper (Gelman GN-6 Meticel 0.45 micron and 25 mm diameter) was placed on top of the agar with the help of a sterile forceps and pressed gently to sit firmly on agar surface leaving no air space in between.

Brilliant Green Medium

| Ingredient | Weight/Volume | |
| --- | --- | --- |
| Peptone | 1.0 g | 1.00% |
| Lactose | 1.0 g | 1.00% |
| Magnesium sulfate | 0.1 g | 0.10% |
| Brilliant green | 0.00125 g | 0.00125% |
| Phenol red | 0.08 g | 0.08% |
| Calcium carbonate | 0.05 g | 0.05% |
| Deionized water pH adjusted to 6.9 | 100 ml | |
| Gellan gum | 0.6 g | 0.60% |

All the ingredients including peptone, lactose, magnesium sulfate, brilliant green, phenol red, calcium carbonate were dissolved in 100 ml of deionized water by heating. The mixture was cooled and pH adjusted to 6.9. Gellan gum (0.6 g) was slowly dispersed to dissolve completely, and the mixture was sterilized for 15 min. at 15 lb. pressure, cooled to 48° C. and poured 4 ml, 6 ml and 8 ml of media in the designated wells. It was allowed to solidify. After solidification, a sterile filter paper (Gelman GN-6) was placed on top of the agar leaving no air space in between.

EMB Medium

| Ingredient | Weight/Volume | |
| --- | --- | --- |
| Peptone | 1.0 g | 1.00% |
| Lactose | 1.0 g | 1.00% |
| Eosin dye | 0.04 g | 0.04% |
| Methylene blue | 0.0065 g | 0.0065% |
| Magnesium sulfate | 0.1 g | 0.10% |
| Deionized water pH adjusted to 7.2 | 100 ml | |
| Gellan gum | 0.6 g | 0.60% |

Peptone, lactose, eosin dye, methylene blue, and magnesium sulfate were weighed and dissolved in 100 ml of deionized water with heating and stirring. The pH was adjusted to 7.2. The medium was heated to boiling and gellan gum (0.6 g) was slowly dispersed to dissolve. It was sterilized for 15 min. at 15 lb. pressure. The medium was cooled to 48° C. and poured 4 ml, 6 ml and 8 ml of media in the designated wells. It was allowed to solidify. After solidification, a sterile filter paper (Gelman GN-6) was placed on top of the agar surface leaving no air space in between.

Cetrimide Base medium

| Ingredient | Weight/Volume | |
| --- | --- | --- |
| Cetrimide | 0.03 g | 0.03% |
| Peptone | 2.0 g | 2.00% |
| Magnesium sulfate | 0.1 g | 0.10% |
| Calcium carbonate | 0.1 g | 0.10% |
| Glycerol | 1.0 ml | 1.00% |
| Deionized Water pH adjusted to 7.2 | 100 ml | |
| Gellan gum | 0.6 g | 0.60% |

Cetrimide, peptone, magnesium sulfate and calcium carbonate were weighed accurately and dissolved in 100 ml of deionized water and 1.0 ml of glycerol with heating and stirring. The pH was adjusted to 7.2. The medium was heated to boiling and gellan gum was slowly dispersed to dissolve completely. It was sterilized for 15 min. at 15 lb. pressure. The medium was cooled to 48° C. and poured 4 ml, 6 ml and 8 ml of media in the designated wells. It was allowed to solidify. After solidification, a sterile filter paper (Gelman GN-6) was placed on top of the agar leaving no air space in between.

Potato Malt Medium

| Ingredient | Weight/Volume | |
| --- | --- | --- |
| Potato starch | 3.0 g | 3.00% |
| Malt | 3.0 g | 3.00% |
| Dextrose | 6.0 g | 6.00% |
| Magnesium sulfate | 0.1 g | 0.10% |
| Deionized water pH was adjusted to 7.4 | 100 ml | |
| Gellan gum | 0.6 g | 0.60% |

Potato starch, malt, dextrose and magnesium sulfate were weighed accurately and dissolved in 100 ml of deionized water with heating and stirring. The pH was adjusted to 7.4. The medium was heated to boiling and gellan gum was slowly dispersed to dissolve. It was sterilized for 15 min. at 15 lb. pressure. The medium was cooled to 48° C. and poured 4 ml, 6 ml and 8 ml of media in the designated wells.

It was allowed to solidify. After solidification, a sterile filter paper (Gelman GN-6) was placed on top of the agar leaving no air space in between.

Streptococcus Medium

| Ingredient | Weight/volume | |
|---|---|---|
| Soytone | 1.0 g | 1.00% |
| Yeast extract | 1.0 g | 1.00% |
| Lactose | 0.1 g | 0.10% |
| Malt extract | 0.2 g | 0.20% |
| Magnesium sulfate | 0.1 g | 0.10% |
| Sodium chloride | 0.50 g | 0.50% |
| Potassium phosphate monobasic | 0.5 g | 0.50% |
| Sodium azide | 0.048 g | 0.048% |
| Bromocresol purple | 0.0015 g | 0.0015% |
| Deionized water pH adjusted to 7.2 | 100 ml | |
| Gellan gum | 0.6 g | 0.60% |
| Triphenyl tetrazolium chloride | 1.0 ml | |

All the ingredients were weighed accuratedly and dissolved in deionized water with the pH adjusted to 7.2 and heated to boiling. Gellan gum (0.6 g) is added slowly with stirring to dissolve. The medium was cooled to 48° C. and add 1.0 ml of 1% triphenyl tetrazolium chloride (TTC). The medium was poured into the designated wells in 4 ml, 6 ml and 8 ml quantities. It was allowed to solidify. After solidification, a sterile filter paper (Gelman GN-6 Meticel 0.45 micron and 25 mm diameter) was placed on top of the agar surface leaving no air space in between.

EXAMPLE 3

Bacterial and fungal suspensions were prepared for the comparative study of the commercial media as described before (Example 1) and the improved nutrient substrates (Example 2) of the present invention. The following bacterial and fungal cultures were used:

1. *Pseudomonas aeruginosa* (ATCC 9027)
2. *Escherichia coil* (ATCC 8739)
3. *Staphylococcus aureus* (ATCC 6538)
4. *Salmonella typhi* (ATCC 6539)
5. *Streptococcus faecalis*
   (*Enterococcus faecalis*) (ATCC 19433)
6. *Aspergillus niger* (ATCC 16404)

All the bacterial cultures #1 to 5 were grown in Penassay seed agar media for 24 h at 35° C. After 24 h, suspensions were made with sterile saline and kept in screw cap bottles. Using Spectronic 20D (at 530 nm 80% absorption), a standardized suspension was made. From this suspension, serial dilutions ($10^{-2}$, $10^{-4}$, $10^{-6}$ & $10^{-8}$) were made and 0.1 ml added to five wells of the hexoid plates.

Fungal suspension of culture #6 was made using saline+ 1% Polysorbate and scrapped well and stored in screw cap bottle. From the suspension using sterile pasteur pipette, 2 drops of suspension was placed on respective agar media in the sixth well.

All plates were covered with the lid and incubated at 35° C. for 24, 48 and 72 hrs. in case of bacteria and 72 hrs. for fungus.

EXAMPLE 4

In order to determine the growth promotion capability of the formulations of the present invention (Example 2) as compared to conventional media tests were made with various test organisms. Bacterial suspensions of 1 ml, 2 ml, 4 ml and 6 ml were used on lyophilized media with sufficient moisture so that bacteria may grow well. It was found that 1 ml, 2 ml and 4 ml does not give enough moisture and 6 ml is too much. The optimum value was found to be 5.5 ml.

From standardized suspension, bacterial suspensions were made by serial dilutions $10^{-2}$, $10^{-4}$, $10^{-6}$ and $10^{-8}$ and kept in screw cap bottles. For fungus *Aspergillus niger* (ATCC 16404), direct suspension was used and no dilutions were made.

5.5 ml. of each suspension was added separately to each designated well in a culture dish containing six wells per dish. The suspension was incubated at 35° C. for 24 hours. Simultaneously, controls were run using 5.5 ml sterile water without any microorganisms under identical conditions. The following changes were observed:

1. Mannitol salt medium—change from red to yellow
2. Brilliant green medium—reddish colony observed
3. EMB medium—metallic sheen observed
4. Centrimide base—bluish green fluorescence observed
5. Potato malt medium—growth of fungus observed
6. Streptococcus medium—reddish colony over blue black background observed.

The color changes are typical for each organism.

EXAMPLE 5

Stability Studies

The formulation of the present invention and commercial media (lyophilized and regular non-lyophilized plates) were stored at room temperature (26° C.) and at 4° C. to test shelf life for six months. Plates are taken off every week and checked with the bacterial and fungal suspensions for their growth. The amount of suspension used for lyophilized plates was 5.5 ml and for regular plates 0.1 ml per well. Control plates were also used containing sterile saline. The results of the first three weeks (21 days) are summarized in Tables 1 and 2 and additional results are shown in Tables 3–10.

The color of the media of the present invention is well defined. The media provided good growth characteristics. The color of the commercial media was not well defined.

TABLE 1

XECHEM FORMULATION PERFORMANCE DATA
(THREE WEEKS STABILITY)

| Description | Temp. Stored at | S. aureus Well no. 1 | P. aeruginosa Well no. 2 | S. typhi Well no. 3 | E. coli Well no. 4 | A. niger Well no. 5 | E. fascalis Well no. 6 |
|---|---|---|---|---|---|---|---|
| REGULAR PLATES | 4° C. | Growth of Bacteria | Growth of Bacteria | Growth of Bacteria | Growth of Bacteria bright | Growth of whitish mycelia | Growth of Bacteria red |

TABLE 1-continued

XECHEM FORMULATION PERFORMANCE DATA
(THREE WEEKS STABILITY)

| | | | | | | | |
|---|---|---|---|---|---|---|---|
| | | well define golden yellow color | fluorescence greenish color bright | reddish colony | metallic sheen | after 48 hrs. | color in blue background |
| | RT. | Golden yellow color well defined. Growth of Bacteria | Fluorescence greenish color bright. Growth of Bacteria | Reddish colony. Growth of Bacteria | Growth of Bacteria. Bright metallic sheen | Growth of whitish mycelia after 48 hr. | Growth of Bacteria. Red color in blue background |
| LYOPHILIZED PLATES | 4° C. | Golden yellow color. Growth of Bacteria | Greenish fluorescence. Growth of Bacteria | Growth of Bacteria. Reddish colony | Growth of Bacteria. Metallic sheen | Growth of whitish mycelia after 48 hr. | Growth of Bacteria. Red color in blue background |
| | RT. | Golden yellow color | Greenish fluorescence | Growth of Bacteria. Reddish colony | Growth of Bacteria. Metallic sheen | Growth of whitish mycelia | Growth of Bacteria. Red color in blue background |
| Description | Temp. Store at | Sterile Saline Well no. 1 | Sterile Saline Well no. 2 | Sterile Saline Well no. 3 | Sterile Saline Well no. 4 | Sterile Saline Well no. 5 | Sterile Saline Well no. 6 |
| CONTROL PLATES | 4° C. | Red Color no change | No change in the media | Greenish Color not changed | Blue Color no metallic sheen | No growth | Blue Color no change |
| | RT. | Red Color no change | No change in the media | Greenish Color not changed | Blue Color no metallic sheen | No growth | Blue Color no change |

TABLE 2

COMMERCIAL FORMULATION PERFORMANCE DATA
(THREE WEEKS STABILITY)

| Description | Temp. Stored at | *S. aureus* Well no. 1 | *P. aeruginosa* Well no. 2 | *S. typhi* Well no. 3 | *E. coli* Well no. 4 | *A. niger* Well no. 5 | *E. fascalis* Well no. 6 |
|---|---|---|---|---|---|---|---|
| REGULAR PLATES | 4° C. | Color changed to yell not bright. Growth moderate | Growth seen fluorescence greenish color not well defined. | Growth is slow reddish colony | Growth seen metallic sheen not bright | Sparse growth of whitish mycelia after 48 hr. | Growth seen red color in blue background |
| | RT. | Growth moderate color changed to yellow not bright | Growth seen fluorescence greenish color not well defined | Growth is slow reddish colony | Growth seen metallic sheen not bright | Growth of whitish mycelia after 48 hr. | Growth seen red color in blue background |
| LYOPHILIZED PLATES | 4° C. | Growth seen yellow color not bright | Growth seen fluorescence greenish color not well defined | Growth slow reddish colony | Growth seen metallic sheen | Sparse growth of whitish mycelia after 48 hr. | Growth of Bacteria red color in blue background |
| | RT. | Growth seen yellow color not bright | Growth seen fluorescence greenish color not well defined | Growth slow reddish colony | Growth seen metallic sheen | Growth of whitish mycelia after 48 hr. | Growth of Bacteria in blue background |
| Description | Temp. Store at | Sterile Saline Well no. 1 | Sterile Saline Well no. 2 | Sterile Saline Well no. 3 | Sterile Saline Well no. 4 | Sterile Saline Well no. 5 | Sterile Saline Well no. 6 |
| CONTROL PLATES | 4° C. | Red Color no change | No change in the media | Greenish Color no changed | Blue Color no metallic sheen | No growth | Blue Color no change |
| | RT. | Red Color no change | No change in the media | Greenish Color no changed | Blue Color no metallic sheen | No growth | Blue Color no change |

TABLE 3

STABILITY STUDIES (4 WEEKS OF STORING)
COMMERCIAL MEDIA

| Organism | Temp. | Well #S | Non lyophilized | Lyophilized |
|---|---|---|---|---|
| S. aureus | RT | 1 | Color red to yellow (24h) | Color red to yellow/light yellow (24h) |
| P. aeruginosa | RT | 2 | Fluorescence (24h) | Fluorescence (24h) |
| S. typhi | RT | 3 | Red colonies | Red colonies |
| E. coli | RT | 4 | Metallic sheen (24h) | Metallic sheen (24h) |
| A. niger | RT | 5 | Growth of mycelia (72h) | Growth of mycelia (72h) |
| E. faecalis | RT | 6 | Blue to red (48h) | Blue to red (48h) |
| S. aureus | 4° C. | 1 | Color red to yellow (24h) | Color red to yellow (24h) |
| P. aeruginosa | 4° C. | 2 | Fluorescence (24h) | Fluorescence (24h) |
| S. typhi | 4° C. | 3 | Red colonies (24h) | Red colonies (24h) |
| E. coli | 4° C. | 4 | Metallic sheen (24h) | Metallic sheen (24h) |
| A. niger | 4° C. | 5 | Growth of mycelia (72h) | Growth of mycelia (72h) |
| E. faecalis | 4° C. | 6 | Blue to red (48h) | Blue to red (48h) |
| Control Sterile Saline | RT | 1 | No color change | No color change |
|  |  | 2 | No color change | No color change |
|  |  | 3 | No color change | No color change |
|  |  | 4 | No color change | No color change |
|  |  | 5 | No color change | No color change |
|  |  | 6 | No color change | No color change |
| Control Sterile Saline | 4° C. | 1 | No color change | No color change |
|  |  | 2 | No color change | No color change |
|  |  | 3 | No color change | No color change |
|  |  | 4 | No color change | No color change |
|  |  | 5 | No color change | No color change |
|  |  | 6 | No color change | No color change |

RT: Room Temperature (26° C.)

TABLE 4

STABILITY STUDIES (4 WEEKS OF STORING)
XECHEM FORMULATIONS

| Organism | Temp. | Well # | Non lyophilized | Lyophilized |
|---|---|---|---|---|
| S. aureus | RT | 1 | Color red to yellow (24h) | Color red to bright yellow |
| P. aeruginosa | RT | 2 | Bright fluorescence | Bright fluorescence |
| S. typhi | RT | 3 | Red colonies | Red colonies |
| E. coli | RT | 4 | Very bright metallic sheen | Very bright metallic sheen |
| A. niger | RT | 5 | Growth of mycelia | Growth of mycelia |
| E. faecalis | RT | 6 | Blue to red colony | Blue to red colony |
| S. aureus | 4° C. | 1 | Color red to bright yellow | Color red to bright yellow |
| P. aeruginosa | 4° C. | 2 | Bright fluorescence | Bright fluorescence |
| S. typhi | 4° C. | 3 | Red colonies | Red colonies |
| E. coli | 4° C. | 4 | Very bright metallic sheen | Very bright metallic sheen |
| A. niger | 4° C. | 5 | Growth of mycelia | Growth of mycelia |
| E. faecalis | 4° C. | 6 | Blue to red colony | Blue to red colony |
| Control (Sterile Saline) | RT | 1 | No color change | No color change |
|  |  | 2 | No color change | No color change |
|  |  | 3 | No color change | No color change |
|  |  | 4 | No color change | No color change |
|  |  | 5 | No color change | No color change |
|  |  | 6 | No color change | No color change |
| Control (Sterile Saline) | 4° C. | 1 | No color change | No color change |
|  |  | 2 | No color change | No color change |
|  |  | 3 | No color change | No color change |
|  |  | 4 | No color change | No color change |
|  |  | 5 | No color change | No color change |
|  |  | 6 | No color change | No color change |

RT: Room temperature (26° C.)

TABLE 5

STABILITY STUDIES (AFTER 5 WEEK STORING)
COMMERCIAL MEDIA

| Organism | Temp. | Well # | Non lyophilized | Lyophilized |
|---|---|---|---|---|
| S. aureus | RT | 1 | Color red to yellow | Color red to light yellow |
| P. aeruginosa | RT | 2 | Fluorescence | Fluorescence |
| S. typhi | RT | 3 | Red colonies | Red colonies |
| E. coli | RT | 4 | Metallic sheen | Metallic sheen |
| A. niger | RT | 5 | Growth of mycelia | Growth of mycelia |
| E. faecalis | RT | 6 | Blue to red color | Blue to red color |
| S. aureus | 4° C. | 1 | Color red to yellow | Color red to light yellow |
| P. aeruginosa | 4° C. | 2 | Fluorescence | Fluorescence |
| S. typhi | 4° C. | 3 | Red colonies | Red colonies |
| E. coli | 4° C. | 4 | Metallic sheen | Metallic sheen |
| A. niger | 4° C. | 5 | Growth of mycelia | Growth of mycelia |
| E. faecalis | 4° C. | 6 | Blue to red colonies | Blue to red colonies |
| Control Sterile Saline | RT | 1 | No color change | No color change |
| | | 2 | No color change | No color change |
| | | 3 | No color change | No color change |
| | | 4 | No color change | No color change |
| | | 5 | No color change | No color change |
| | | 6 | No color change | No color change |
| Control (Sterile Saline) | 4° C. | 1 | No color change | No color change |
| | | 2 | No color change | No color change |
| | | 3 | No color change | No color change |
| | | 4 | No color change | No color change |
| | | 5 | No color change | No color change |
| | | 6 | No color change | No color change |

TABLE 6

STABILITY STUDIES (AFTER 5 WEEK STORING)
XECHEM FORMULATIONS

| Organism | Temp. | Well # | Non lyophilized | Lyophilized |
|---|---|---|---|---|
| S. aureus | RT | 1 | Color red to bright yellow | Color red to bright yellow |
| P. aeruginosa | RT | 2 | Bright fluorescence | Bright fluorescence |
| S. typhi | RT | 3 | Red colonies | Red colonies |
| E. coli | RT | 4 | Very bright metallic sheen | Very bright metallic sheen |
| A. niger | RT | 3 | Growth of mycelia | Growth of mycelia |
| E. faecalis | RT | 6 | Blue to red colonies | Blue to red colonies |
| S. aureus | 4° C. | 1 | Color red to bright yellow | Color red to bright yellow |
| P. aeruginosa | 4° C. | 2 | Bright fluorescence | Bright fluorescence |
| S. typhi | 4° C. | 3 | Red colonies | Red colonies |
| E. coli | 4° C. | 4 | Very bright metallic sheen | Very bright metallic sheen |
| A. niger | 4° C. | 5 | Growth of mycelia | Growth of mycelia |
| E. faecalis | 4° C. | 6 | Blue to red colony | Blue to red colony |
| Control (Sterile Saline) | RT | 1 | No color change | No color change |
| | | 2 | No color change | No color change |
| | | 3 | No color change | No color change |
| | | 4 | No color change | No color change |
| | | 5 | No color change | No color change |
| | | 6 | No color change | No color change |
| Control Sterile Saline | 4° C. | 1 | No color change | No color change |
| | | 2 | No color change | No color change |
| | | 3 | No color change | No color change |
| | | 4 | No color change | No color change |
| | | 5 | No color change | No color change |
| | | 6 | No color change | No color change |

TABLE 7

STABILITY STUDIES (AFTER 6 WEEKS STORING)
COMMERCIAL MEDIA

| Organism | Temp. | Well # | Non lyophilized | Lyophilized |
| --- | --- | --- | --- | --- |
| S. aureus | RT | 1 | Color red to yellow | Color red to yellow |
| P. aeruginosa | RT | 2 | Fluorescence | Fluorescence |
| S. typhi | RT | 3 | Red colonies | Red colonies |
| E coli | RT | 4 | Metallic sheen | Metallic sheen |
| A. niger | RT | 5 | Growth of mycelia | Growth of mycelia |
| E. faecalis | RT | 6 | Blue to red colonies | Blue to red colonies |
| S. aureus | 4° C. | 1 | Color red to yellow | Color red to yellow |
| P. aeruginosa | 4° C. | 2 | Fluorescence | Fluorescence |
| S. typhi | 4° C. | 3 | Red colonies | Red colonies |
| E. coli | 4° C. | 4 | Metallic sheen | Metallic sheen |
| A. niger | 4° C. | 5 | Growth of mycelia | Growth of mycelia |
| E. faecalis | 4° C. | 6 | Blue to red colonies | Blue to red colonies |
| Control Sterile Saline | RT | 1 | No color change | No color change |
| | | 2 | No color change | No color change |
| | | 3 | No color change | No color change |
| | | 4 | No color change | No color change |
| | | 5 | No color change | No color change |
| | | 6 | No color change | No color change |
| Control Sterile Saline | 4° C. | 1 | No color change | No color change |
| | | 2 | No color change | No color change |
| | | 3 | No color change | No color change |
| | | 4 | No color change | No color change |
| | | 5 | No color change | No color change |
| | | 6 | No color change | No color change |

TABLE 8

STABILITY STUDIES (AFTER 6 WEEKS STORING)
XECHEM FORMULATIONS

| Organism | Temp. | Well # | Non lyophilized | Lyophilized |
| --- | --- | --- | --- | --- |
| S. aureus | RT | 1 | Color red to bright yellow | Color red to bright yellow |
| P. aeruginosa | RT | 2 | Bright fluorescence | Bright fluorescence |
| S. typhi | RT | 3 | Red colonies | Red colonies |
| E. coli | RT | 4 | Very bright metallic sheen | Very bright metallic sheen |
| A. niger | RT | 5 | Growth of mycelia | Sporulation and Mycelial growth |
| E. faecalis | RT | 6 | Blue to red colonies | Blue to red colonies |
| S. aureus | 4° C. | 1 | Color red to bright yellow | Color red to bright yellow |
| P. aeruginosa | 4° C. | 2 | Bright fluorescence | Bright fluorescence |
| S. typhi | 4° C. | 3 | Red colonies | Red colonies |
| E. coli | 4° C. | 4 | Very bright metallic sheen | Very bright metallic sheen |
| A. niger | 4° C. | 5 | Growth of mycelia | Sporulation and Mycelial growth |
| E. faecalis | 4° C. | 6 | Blue to red colonies | Blue to red colonies |
| Control (Sterile Saline) | RT | 1 | No color change | No color change |
| | | 2 | No color change | No color change |
| | | 3 | No color change | No color change |
| | | 4 | No color change | No color change |
| | | 5 | No color change | No color change |
| | | 6 | No color change | No color change |
| Control Sterile Saline | 4° C. | 1 | No color change | No color change |
| | | 2 | No color change | No color change |
| | | 3 | No color change | No color change |
| | | 4 | No color change | No color change |
| | | 5 | No color change | No color change |
| | | 6 | No color change | No color change |

TABLE 9

STABILITY STUDIES OF HEXOID PLATES FOR 7TH, 8TH, 9TH & 10TH WEEK.

| Description | Temp | 7th week of storing | | | | | | 8th week of storing | | | | | |
|---|---|---|---|---|---|---|---|---|---|---|---|---|---|
| | | W1 | W2 | W3 | W4 | W5 | W6 | W1 | W2 | W3 | W4 | W5 | W6 |
| Commercial Non lyophilized | RT | 1, Y | 2, G | 3, R | 4, S | 5, M | 6, R | 1, Y | 2, G | 3, R | 4, S | 5, M | 6, R |
| Commercial Lyophilized | RT | 1, Y | 2, G | 3, R | 4, S | 5, S&M | 6, R | 1, Y | 2, G | 3, R | 4, S | 5, S&M | 6,R |
| Commercial Non lyophilized | 4° C. | 1, Y | 2, G | 3, R | 4, S | 5, M | 6, R | 1, Y | 2, G | 3, R | 4, S | 5, M | 6, R |
| Commercial Lyophilized | 4° C. | 1, Y | 2, G | 3, R | 4, S | 5, S&M | 6, R | 1, Y | 2, G | 3, R | 4, S | 5, S&M | 6, R |
| Xechem Non lyophilized | RT | 1, BY | 2, BG | 3, R | 4, BS | 5, M | 6, R | 1, BY | 2, BG | 3, R | 4, BS | 5, M | 6, R |
| Xechem Lyophilized | RT | 1, BY | 2, BG | 3, R | 4, BS | 5, S&M | 6, R | 1, BY | 2, BG | 3, R | 4, BS | 5, S&M | 6, R |
| Xechem Non lyophilized | 4° C. | 1, BY | 2, BG | 3, R | 4, BS | 5, M | 6, R | 1, BY | 2, BG | 3, R | 4, BS | 5, M | 6, R |
| Xechem Lyophilized | 4° C. | 1, BY | 2, BG | 3, R | 4, BS | 5, S&M | 6, R | 1, BY | 2, BG | 3, R | 4, BS | 5, S&M | 6, R |
| Control Non lyophilized | RT | NC | NC | NC | NC | NC | NC | NC | NC | NC | NC | NC | NC |
| Control Lyophilized | RT | NC | NC | NC | NC | NC | NC | NC | NC | NC | NC | NC | NC |
| Control Non lyophilized | 4° C. | NC | NC | NC | NC | NC | NC | NC | NC | NC | NC | NC | NC |
| Control Lyophilized | 4° C. | NC | NC | NC | NC | NC | NC | NC | NC | NC | NC | NC | NC |

| Description | Temp | 9th week of storing | | | | | | 10th week of storing | | | | | |
|---|---|---|---|---|---|---|---|---|---|---|---|---|---|
| | | W1 | W2 | W3 | W4 | W5 | W6 | W1 | W2 | W3 | W4 | W5 | W6 |
| Commercial Non lyophilized | RT | 1, Y | 2, G | 3, R | 4, S | 5, M | 6, R | 1, Y | 2, G | 3, R | 4, S | 5, M | 6, R |
| Commercial Lyophilized | RT | 1, Y | 2, G | 3, R | 4, S | 5, S&M | 6, R | 1, Y | 2, G | 3, R | 4, S | 5, S&M | 6, R |
| Commercial Non lyophilized | 4° C. | 1, Y | 2, G | 3, R | 4, S | 5, M | 6, R | 1, Y | 2, G | 3, R | 4, S | 5, M | 6, R |
| Commercial Lyophilized | 4° C. | 1, Y | 2, G | 3, R | 4, S | 5, S&M | 6, R | 1, Y | 2, G | 3, R | 4, S | 5, S&M | 6, R |
| Xechem Non lyophilized | RT | 1, BY | 2, BG | 3, R | 4, BS | 5, M | 6, R | 1, BY | 2, BG | 3, R | 4, BS | 5, M | 6, R |
| Xechem Lyophilized | RT | 1, BY | 2, BG | 3, R | 4, BS | 5, S&M | 6, R | 1, BY | 2, BG | 3, R | 4, BS | 5, S&M | 6, R |
| Xechem Non lyophilized | 4° C. | 1, BY | 2, BG | 3, R | 4, BS | 5, M | 6, R | 1, BY | 2, BG | 3, R | 4, BS | 5, M | 6, R |
| Xechem Lyophilized | 4° C. | 1, BY | 2, BG | 3, R | 4, BS | 5, S&M | 6, R | 1, BY | 2, BG | 3, R | 4, BS | 5, S&M | 6, R |
| Control Non lyophilized | RT | NC | NC | NC | NC | NC | NC | NC | NC | NC | NC | NC | NC |
| Control Lyophilized | RT | NC | NC | NC | NC | NC | NC | NC | NC | NC | NC | NC | NC |
| Control Non lyophilized | 4° C. | NC | NC | NC | NC | NC | NC | NC | NC | NC | NC | NC | NC |
| Control Lyophilized | 4° C. | NC | NC | NC | NC | NC | NC | NC | NC | NC | NC | NC | NC |

1 - *Staphylococcus aureus*
2 - *Pseudomonas aeruginosa*
3 - *Salmonella typhi*
4 - *Escherichia coli*
5 - *Aspergillus niger*
6 - *Enterococcus faecalis*
Y - color changed to yellow
G - color changed to green fluorescence
R - color changed to red
S - color changed to metallic sheen
M - mycelia growth
S&M - spore & mycelia growth
BY - color changed to bright yellow
BG - color changed to bright green fluorescence
BS - color changed to bright metallic sheen
NC - no color change

TABLE 10

STABILITY STUDIES OF QUALTURE PLATES FOR 7TH, 8TH, 9TH, & 10TH WEEK.

|  |  | 7th week | | | | 8th week | | | | 9th week | | | | 10th week | | | |
|---|---|---|---|---|---|---|---|---|---|---|---|---|---|---|---|---|---|
| Description | | Q1 | Q2 | Q3 | Q4 | Q1 | Q2 | Q3 | Q4 | Q1 | Q2 | Q3 | Q4 | Q1 | Q2 | Q3 | Q4 |
| RT | SA | Y | NC | DB | LY | Y | NC | DB | LY | Y | NC | B | G | Y | NC | DD | Y |
|  | PA | R | B | P | P | B | B | P | P | PR | PR | R | P | B | PR | P | R |
|  | ST | Y | NC | PR | B | Y | NC | PR | B | PR | NC | R | P | B | Y | P | R&Y |
|  | EC | NC | Y | R | P | NC | Y | R | P | PR | R&Y | R | Y | LY | Y&C | R | Y |
|  | AN | F | F | F | F | F | P | F | F | F | F | F | F | F | F | F | F |
|  | EF | NC | NC | PR | R&Y | NC | NC | PR | R&Y | Y | NC | B | Y&G | Y | NC | PR | Y&G |
| 4° C. | SA | Y | NC | DB | LY | Y | NC | DB | LY | Y | NC | B | G | Y | NC | DB | NC |
|  | PA | B | PR | R | P | B | PR | R | P | PR | PR | R | P | B | PR | P | R |
|  | ST | LY | NC | PR | B&Y | LY | NC | PR | B&Y | PR | NC | R | P | B | Y | PR | R&Y |
|  | EC | NC | Y | R | P | NC | Y | R | P | PR | R&Y | R | Y&G | LY | Y | R | Y |
|  | AN | F | F | F | F | F | F | F | F | F | F | F | F | F | F | F | F |
|  | EF | NC | NC | PR | R&Y | NC | NC | PR | R&Y | Y | NC | B | Y&F | B | Beige | R | P |
| Control RT | | Y | NC | B | Y | Y | NC | B | Y | Y | NC | PR | Y&R | G | NC | B | P |
| Control 4° C. | | Y | NC | B | Y | Y | NC | B | Y | Y | NC | PR | Y&G | G | NC | B | P |

SA - *Staphylococcus aureus*
PA - *Pseudomonas aeruginosa*
ST - *Salmonella typhi*
EC - *Escherichia coli*
AN - *Aspergillus niger*
EF - *Enterococcus faecalis*
Y - Yellow
NC - No Color Change
DB - Deep Blue
LY - Light Yellow
B - Blue
P - Pink
PR - Purple
R&Y - Red & Yellow
B&Y - Blue & Yellow
F - Fungal growth
G - Green
Y&G - Yellow & Green In order to use the nutrient substrate carrier or media of the present invention, the lid 12 or 62 of the device 10 is removed. The liquid or dry nutrient substrate carrier or media is inserted into wells 16. Lid 12 or 62 is placed in position. If a dry nutrient substrate carrier or media is used, it is reconstituted by adding water through the aperture 52 or 60 or by the water present in the specimen sample. Likewise, the specimen(s) is then placed through aperture 52 or 60 and the appropriate channel 64 by a curved sampling probe. After incubation, visual observation and evaluation can take place in the customary manner. The bright, rich, full color of the nutrient substrate carrier or media of the present invention allows for easy identification of the microorganism(s).

While a preferred embodiment of the device, method and nutrient substrate have been shown, it is to be understood that they are illustrative and not limitative of the present invention.

What is claimed is:

1. A device for use in culturing and identifying microorganisms comprising:

a base having formed within it a plurality of wells for receiving media and specimens, the base being transparent and having a front end and a back end, a transparent lid for covering the base and the wells therein, the lid having a front end and a back end, an exterior side and an interior side, the lid having means for fluid communication with the wells from the exterior side of the lid to the wells wherein the means for enabling communication in the device is a centrally positioned aperture connected to a plurality of channels, each of the channels extending through the lid to be positioned above each well in the base.

2. The device of claim 1 wherein the wells in the base are placed within a platform on the base.

3. The device of claim 1 wherein the front end of the lid engages the front end of the base in only one position to ensure sealing of the device.

4. The device of claim 1 wherein the plurality of channels radiate from the centrally positioned aperture.

\* \* \* \* \*